United States Patent [19]

Galante

[11] 4,384,058
[45] May 17, 1983

[54] NAIL LACQUER COMPOSITIONS

[75] Inventor: Gary Galante, Ramsey, N.J.

[73] Assignee: Avon Products, Inc., Suffern, N.Y.

[21] Appl. No.: 246,775

[22] Filed: Mar. 23, 1981

Related U.S. Application Data

[63] Continuation of Ser. No. 100,192, Dec. 4, 1979, abandoned.

[51] Int. Cl.$^3$ ................................................ A61K 7/04
[52] U.S. Cl. ..................................... 524/32; 106/195; 424/61
[58] Field of Search .......................... 424/61; 106/195; 260/17 R; 524/32

[56] References Cited

U.S. PATENT DOCUMENTS 3,849,547 11/1974 Kalopissis .............................. 424/61
4,126,675 11/1978 Boulogne et al. ..................... 424/61

OTHER PUBLICATIONS

Cosmetic Technology, "Nail–Enamel Resins", (10–1979), pp. 53–55.

*Primary Examiner*—Lorenzo B. Hayes
*Attorney, Agent, or Firm*—Sigalos & Levine

[57] ABSTRACT

A nail lacquer composition comprising a film-forming agent, a compatible solvent, and an auxiliary resin present in an amount sufficient to increase the wear resistance of the composition when dry and selected from alkyl cyanoacrylates, styrene-acrylonitrile-acrylic terpolymers, or mixtures thereof.

4 Claims, No Drawings

NAIL LACQUER COMPOSITIONS

This is a continuation of application Ser. No. 100,192, filed Dec. 4, 1979, now abandoned.

BACKGROUND OF THE INVENTION

Two of the most important characteristics of all nail lacquer compositions are their gloss and wear properties after being applied to the nail of the user. The highest gloss possible and maximum resistance to wear, such as scuffing and chipping, are constantly sought after.

Since almost all conventionally used nail lacquer compositions are nitrocellulose-based, i.e., use nitrocellulose as the sole or major film-forming agent, efforts to improve the gloss and wear of such compositions has included the addition of compatible modifier resins. While resins, such as p-toulene-sulfonamide-formaldehyde, have been generally satisfactorily used for this purpose, the gloss and wear properties have not reached the optimum levels desired. In general, both natural and synthetic resins have been tried and found wanting.

SUMMARY OF THE INVENTION

The instant invention provides nail lacquer compositions having wear properties improved over the conventional, presently used compositions.

Briefly, the present invention comprises nail lacquer compositions comprising a film-forming agent, a compatible solvent and an auxiliary resin present in an amount sufficient to increase the wear resistance of the composition when dry and selected from alkyl cyanoacrylates, styrene-acrylonitrile-acrylic terpolymers, or mixtures thereof.

DETAILED DESCRIPTION

As used herein the term "nail lacquer" is intended to be synonymous with nail enamels and to mean and include all film-forming nail coatings, such as base coats, top coats, nail strengtheners, nail menders, clear nail lacquers, and pigmented, cream, and frost nail lacquers, and the like.

For purposes of further description of the invention, it will be discussed in terms of a pigmented composition, it being understood that the invention is applicable to all nail lacquer compositions.

The compositions of the present invention require the utilization of an auxiliary resin in order to obtain improved wear and in the case of the terpolymers, as discussed below, also improved gloss. Such auxiliary resins must be a film-forming alkyl cyanoacrylate, a film-forming styrene-acrylonitrile-acrylic terpolymer, or a mixture thereof.

As to the alkyl cyanoacrylates, any film-forming resin can be used, such as methyl or ethyl cyanoacrylate. Such resins are commercially available from Loctite Corporation as LOCTITE 916 and LOCTITE 918. Such cyanoacrylates have been used in other applications as adhesives and give increased wear properties to nail enamels containing the same, but no positive effects as to gloss.

With respect to the styrene-acrylonitrile-acrylic terpolymers, these are available from Polyvinyl Chemical Industries under the name NEOCRYL B-1000. They are available as free-flowing beads or as 40% solids solution in toluene and are soluble in the solvents commonly used in nail lacquers. The precise chemical formulation of these NEOCRYL B-1000 resins is not presently known since they are being maintained as trade secrets by the manufacturers thereof. The terpolymers give both increased gloss and improved wear properties and are the preferred auxiliary resins.

Both the cyanoacrylates and terpolymers are compatible with nitrocellulose and other resins commonly used to modify the nail lacquer compositions. This is important since it permits the addition of the cyanoacrylates and/or terpolymers to the conventional and well-known nitrocellulose-based nail lacquer compositions to increase their gloss and wear properties.

Conventional nitrocellulose-based pigmented nail lacquer compositions comprise nitrocellulose as the main film-forming resin, a modifying resin, plasticizers, a pigment, a thixotropic agent for suspending the pigment, solvents, and an alcohol. The solvent, usually a mixture of solvents such as n-butyl acetate, ethyl acetate, and toluene, comprises the major percentages by weight of the composition; usually at least about 60% by weight. The nitrocellulose and any modifier resin, such as an aryl-sulfonamide-formaldehyde resin, form the next largest component, followed by the alcohol, plasticizers for the nitrocellulose (such as dibutyl phthalate and/or camphor), thixotropic-agent, and pigment.

The auxiliary film-forming resins of the present invention can be added directly to such compositions or in place of the modifying resin. As to proportions, from about 2 to 12% by weight of the auxiliary resin, based on the total weight of the nail lacquer composition; can be used; about 5% by weight being preferred. While either the cyanoacrylate or terpolymer can be added alone in the amounts noted, a combination thereof can be used. In such combinations, if both optimum gloss and wear properties are desired, the cyanoacrylate should not be used in an amount more than 50% by weight of the combination. The proportions of the other components in the nail lacquer composition are those usually employed.

While, as previously noted, the instant invention has been described in connection with a pigmented nail lacquer, it is applicable to all nail lacquer compositions. The amount of the auxiliary resin noted above as suitable in pigmented nail lacquers is equally suitable with the other nail lacquers.

While this invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A nail lacquer composition consisting essentially of a film-forming agent comprising nitrocellulose as the major component, a compatible solvent, and a styrene-acrylonitrile-acrylic terpolymer in an amount sufficient to increase the gloss and wear resistance of the composition when dry.

2. The composition of claim 1 wherein said compatible solvent is an ester solvent.

3. The composition of claims 1 or 2, wherein the terpolymer is present in an amount of from about 2 to 12% by weight, based on the total weight of the composition.

4. A nail lacquer composition consisting essentially of nitrocellulose, at least one ester solvent, and a styrene-acrylonitrile-acrylic terpolymer, said terpolymer being present in an amount of from about 2 to 12% by weight, based on the total weight of the composition.

* * * * *